(12) United States Patent
Walters

(10) Patent No.: US 9,439,913 B1
(45) Date of Patent: Sep. 13, 2016

(54) FAT-SOLUBLE VITAMIN FORMULATIONS

(71) Applicant: Michael J. Walters, Huntsville, AL (US)

(72) Inventor: Michael J. Walters, Huntsville, AL (US)

(73) Assignee: MVW Nutritionals, Inc., Huntsville, AL (US)

( * ) Notice: Subject to any disclaimer, the term of this patent is extended or adjusted under 35 U.S.C. 154(b) by 0 days.

(21) Appl. No.: 14/278,794

(22) Filed: May 15, 2014

Related U.S. Application Data

(60) Provisional application No. 61/904,505, filed on Nov. 15, 2013.

(51) Int. Cl.
  *A61K 31/59* (2006.01)
  *A61K 31/593* (2006.01)
  *A61K 31/122* (2006.01)
  *A61K 47/44* (2006.01)
  *A61K 31/315* (2006.01)

(52) U.S. Cl.
  CPC ........... *A61K 31/593* (2013.01); *A61K 31/122* (2013.01); *A61K 31/315* (2013.01); *A61K 47/44* (2013.01)

(58) Field of Classification Search
  CPC . A61K 31/315; A61K 31/592; A61K 31/593
  USPC ....................................... 514/167
  See application file for complete search history.

(56) References Cited

U.S. PATENT DOCUMENTS 8,617,617 B2 * 12/2013 Giordano ............... A61K 31/07
424/638

FOREIGN PATENT DOCUMENTS

TR WO 2011152810 A1 * 12/2011 ........... A61K 9/0007

OTHER PUBLICATIONS

Borowitz D., et al. Consensus Report on Nutrition for Pediatric Patients With Cystic Fibrosis, J Pediatr Gastroenterol Nutr Sep. 2002, 35(3):246-259.
Holick, MF, et al. Evaluation, Treatment, and Prevention of Vitamin D Deficiency: An Endocrine Society Clinical Practice Guideline, J Clin Endocrinol Metab, Jul. 2011, 96(7):1911-1930.
Lam, HS, et al. Risk of Vitamin A Toxicity from Candy-Like Chewable Vitamin Supplements for Children, Pediatrics, Aug. 2006,118:820-824.
Tangpricha V., et al. An Update on the Screening, Diagnosis, Management, and Treatment of Vitamin D Deficiency in Individuals with Cystic Fibrosis: Evidence-Based Recommendations from the Cystic Fibrosis Foundation, J Clin Endocrinol Metab, Apr. 2012, 97(4):1082-1093.

\* cited by examiner

*Primary Examiner* — Kevin E Weddington
(74) *Attorney, Agent, or Firm* — Maynard Cooper & Gale, P.C.; Matthew J. Parker

(57) ABSTRACT

The present disclosure generally pertains to formulations containing two or more fat-soluble vitamins, lemon oil, and zinc. Also disclosed are kits containing such formulations and methods for administering such formulations to treat malabsorption in subjects diagnosed with CF, Crohn's Disease, Colitis, Irritable Bowel Syndrome, Celiac Disease, and other like conditions.

11 Claims, No Drawings

FAT-SOLUBLE VITAMIN FORMULATIONS

CROSS REFERENCE TO RELATED APPLICATION

This application claims priority to U.S. Provisional Patent Application No. 61/904,505, entitled "CF-Specific Oral Daily Multivitamin Formulations for Chronic Use Containing Increased Serving Sizes of Vitamin D" and filed on Nov. 15, 2013, which is incorporated herein by reference.

RELATED ART

Subjects with malabsorption often have a diminished ability to absorb fat-soluble vitamins (A, D, E, and K). Vitamin D deficiency, for example, is common in patients with cystic fibrosis ("CF"), a condition characterized by malabsorption. This deficiency is associated with decreased bone mass in children, failure to achieve expected peak bone mass in young adults, and osteoporosis in mature adults [1]. Further, Vitamin D deficiency may impact other co-morbidities associated with CF.

As a result, the treatment of malabsorption in a subject includes supplementation through the intake of daily oral multivitamin formulations containing water-soluble and fat-soluble vitamins and their derivatives, often with ingredients such as zinc. Due to the subjects' poor absorption, such multivitamin formulations typically contain elevated levels of fat-soluble vitamins compared with the levels of conventional multivitamins. The elevated levels of fat-soluble vitamins in such multivitamins often induce belching as an unintended side effect, which may reduce a subject's compliance with a vitamin regimen.

Subjects with malabsorption face an additional difficulty due to the different levels of fat-soluble vitamins that are required for particular conditions. The CF Foundation [1] and the Endocrine Society [2], for example, recently provided new recommendations for CF patients to supplement their intake of Vitamin D, suggesting that Vitamin D amounts in the range of 3000-5000 IUs/day may be needed for most adults with CF, which may be dosed daily or weekly. Despite these recommendations, no CF-specific multivitamin formulation currently contains sufficient levels of Vitamin D in a single serving. Increasing the number of servings of currently-available CF multivitamin to achieve these recommendations would result in excess levels of other fat-soluble vitamins (A, E, K) which are potentially toxic when part of a chronic regimen. An overdose of Vitamins A, E, or K can cause serious or life-threatening side effects if taken in excessive doses, including stomach pain, vomiting, diarrhea, constipation, loss of appetite, hair loss, peeling skin, tingly feeling in or around the mouth, changes in menstrual periods, weight loss, severe headache, muscle or joint pain, severe back pain, blood in urine, pale skin, and facilitated bruising or bleeding [3].

Vitamin-specific supplementation within CF Foundation and Endocrine Society guidelines is recommended to avoid the buildup of excess fat-soluble vitamins and their associated toxicity. Without a single multivitamin containing the necessary concentrations of particular vitamins, however, subjects must supplement their multivitamins with one or more vitamin-specific supplements, resulting in pill burden and a potential drop in compliance with the vitamin regimen. In the treatment of CF, for example, adherence to recommended Vitamin D levels requires the intake of additional pills or liquid forms of Vitamin D in addition to currently-available CF multivitamins, because no CF-specific multivitamin is available with the recommended amounts of Vitamin D, particularly Vitamin $D_3$, as a single formulation.

Compliance with the recommended intake of vitamins remains a challenge for patients with malabsorption, due to pill burden and belching induced by elevated doses of fat-soluble vitamins.

DETAILED DESCRIPTION

The present disclosure generally pertains to formulations containing two or more fat-soluble vitamins, lemon oil, and zinc. Also disclosed are kits containing such formulations and methods for administering such formulations to treat malabsorption in subjects diagnosed with CF, Crohn's Disease, Colitis, Irritable Bowel Syndrome, Celiac Disease, and other like conditions.

As used herein, the term "about" means plus or minus approximately ten percent (10%) of the indicated value, such that "about 3000 IUs" indicates approximately 2700 to 3300 IUs.

As used herein, the term "administer" means the act of delivering or applying a formulation to a subject. For example, administration of a formulation to a subject includes, but is not limited to, oral consumption, intravenous injection, and topical application.

As used herein, "dose" means a specified quantity of a formulation provided in a single administration or over a specified amount of time. In certain embodiments, a dose may be administered in two or more boluses, tablets, soft gels, drops, or other known vehicles.

As used herein, the term "excipient" means an additive included in the final dosage vehicle of a formulation. Excipients provide physical and/or aesthetic properties of the dosage vehicle for delivery of the formulation to the desired target location.

As used herein, the term "formulation" means a preparation suitable for administration to a subject.

As used herein, the term "kit" means a collection of formulations in discrete dosage unit forms.

As used herein, "lubricant" means a substance that reduces friction between a formulation and the surfaces of an apparatus used to compact the formulation into a compressed form. Suitable lubricants include, for example, fatty acids, such as palmitic acid, stearic acid, oleic acid, hydrogenated vegetable oils, triglycerides of fatty acids, metal salts of fatty acids, such as for example, zinc stearate and magnesium stearate, glycols, such as polyethylene glycol, and talc, as well as mixtures thereof.

As used herein, the term "subject" means any and all organisms. "Subject" may refer to a human or any other animal. "Subject" may also refer to a fetus.

The present disclosure contemplates a formulation containing Vitamin D, at least one additional fat-soluble vitamin, lemon oil, and zinc. The formulation may also include one or more water-soluble vitamins. The formulations may be encapsulated in a soft gel, in a chewable tablet, in a water-miscible drop, or other known vehicles.

Examples of fat-soluble vitamins contemplated in the present disclosure include Vitamins A, D, E, K, and the like. It is to be understood that the presently-described formulations are not limited to these vitamins and may include other vitamins in additional embodiments.

Examples of Vitamin A include retinol (Vitamin $A_1$), 3-dehydroretinol (Vitamin $A_2$), beta-carotene, retinal, 3-dehydroretinal, retinoic acid, 3-dehydroretinoic acid, derivatives thereof such as acetate esters, palmitate esters, and the like. In certain embodiments, the present disclosure contemplates a formulation with a concentration of Vitamin A of at least 4600 IUs. In other embodiments, the Vitamin A concentration is about 4600, 9200, or 16000 IUs. In an additional embodiment, the Vitamin A may include two or more forms of Vitamin A, for example retinol and beta-carotene.

Examples of Vitamin D include ergocalciferol (Vitamin $D_2$), cholecalciferol (Vitamin $D_3$), derivatives thereof such as sulfate esters, and the like. In one embodiment, the Vitamin D is in the form of Vitamin $D_3$. In certain embodiments, the present disclosure contemplates a formulation with a Vitamin D concentration of at least 1500 IUs. In other embodiments, the Vitamin D concentration is about 1500, 3000, or 5000 IUs. In an additional embodiment, the formulation may have a Vitamin D concentration determined according to Table I, below, based on the 'routine dosing' for a subject's age. In an additional embodiment, the Vitamin D concentration is determined according to the 'step 1' dose in Table I for a subject's age where a physician has determined the subject has a Vitamin D deficiency. In an additional embodiment, the Vitamin D concentration is determined according to the 'step 2' dose in Table I for a subject's age where a physician has determined the subject has a Vitamin D deficiency despite the prior administration of a 'step 1' dose.

TABLE I

Recommended Vitamin D Intake for Children and Adults with CF and Vitamin D Deficiency.

| Age (years) | Routine Dosing with CF-Specific Vitamins (IUs) | Step 1: Dose Increases (IUs) | Step 2: Dose Titration Maximum (IUs) |
|---|---|---|---|
| ≤1 | 400-500 | 800-1000 | ≤2000 |
| >1 to 10 | 800-1000 | 1600-3000 | ≤4000 |
| >10 to 18 | 800-2000 | 1600-6000 | ≤10000 |
| >18 | 800-2000 | 1600-6000 | ≤10000 |

Examples of Vitamin E include alpha-tocopherol, beta-tocopherol, gamma-tocopherol, delta-tocopherol, alpha-tocotrienol, beta-tocotrienol, gamma-tocotrienol, delta-tocotrienol, derivatives thereof such as acetate esters, nicotinate esters, phosphate esters, and the like. Salts thereof may also be included, for example, alpha-tocopherol disodium salt is included. In certain embodiments, the present disclosure contemplates a formulation with a Vitamin E concentration of at least 100 IUs. In other embodiments, the Vitamin E concentration is about 100 or 200 IUs.

Examples of Vitamin K include phylloquinone (Vitamin $K_1$), menaquinone (Vitamin $K_2$), menadione (Vitamin $K_3$), Vitamin $K_4$, Vitamin $K_5$, derivatives thereof, and the like. In certain embodiments, the present disclosure contemplates a formulation with a Vitamin K concentration of greater than 800 mcg. In other embodiments, the Vitamin K concentration is about 1000 or 2000 mcg. The Vitamin K may include two or more forms of Vitamin K, for example phylloquinone and menaquinone.

Examples of water-soluble vitamins contemplated in the present disclosure include Vitamins B, C, and the like.

Examples of Vitamin B include: thiamine (Vitamin $B_1$); riboflavin (Vitamin $B_2$); niacin and niacinamide (Vitamin $B_3$); pantothenic acid (Vitamin $B_5$); pyridoxine, pyridoxamine, and pyridoxal (Vitamin $B_6$); biotin (Vitamin $B_7$); folic acid and folinic acid (Vitamin $B_9$); and cyanocobalamin, hydroxycobalamin, and methylcobalamin (Vitamin $B_{12}$), salts and derivatives thereof, and the like. In certain embodiments, the present disclosure contemplates a formulation with Vitamin B, where such Vitamin B may include two or more forms of Vitamin B, for example riboflavin and folic acid.

Examples of Vitamin C include ascorbic acid, salts thereof, such as zinc ascorbate and sodium ascorbate, derivatives thereof, and the like. In certain embodiments, the present disclosure contemplates a formulation with Vitamin C, where such Vitamin C may include two or more forms of Vitamin C, for example zinc ascorbate and ascorbic acid.

The fat-soluble and water-soluble vitamins contemplated by the present disclosure may be obtained by extraction and purification from a natural source by a method known in the art, chemical synthesis by a method known in the art, or a fermentation method known in the art using microorganisms or the like. Alternatively, commercially-available fat-soluble and water-soluble vitamins are contemplated.

Examples of zinc include zinc ascorbate, zing gluconate, zinc oxide, and the like. In certain embodiments, the present disclosure contemplates a formulation with two or more forms of zinc, for example zinc ascorbate and zinc oxide.

In certain embodiments, the present disclosure contemplates a formulation in single dosage vehicle suitable for ingestion by a subject. Without limitation, exemplary dosage vehicles include soft gels, chewable tablets, water-miscible drops, lozenges, gel caps, and syrups, made by processes known in the art.

Generally, soft gels may be formed by blending the ingredients and subsequently filling the soft gel with the blended ingredients using conventional automatic filling equipment. For example, a soft gel may be prepared by dispersing the formulation in an appropriate vehicle, such as vegetable oil, to form a high-viscosity mixture. This mixture is then encapsulated with a gelatin-based film using technology and machinery known in the art. The soft gel may be further processed as desired. For example, the soft gel may include specific coatings designed to optimize survival of the formulation in the stomach and to prevent gastro-intestinal tract upset. Such coatings may enhance absorption and bioavailability of the formulation. Some subjects may have difficulties in swallowing a hard, solid tablet, especially children and adults having small oral and pharyngeal cavities. The soft gel may be limited in volume to facilitate the ability of such subjects to swallow it.

In certain embodiments, the present disclosure contemplates a formulation encapsulated in a soft gel with excipients including gelatin, purified water, glycerin, soybean oil, natural lemon flavor, beeswax, soy lecithin, polysorbate 80, sucralose, and caramel color. In certain embodiments, the formulation encapsulated in a soft gel is no greater than 2.0 mL total volume.

Generally, chewable tablets may be formed by a compactable granular formulation. A chewable form of a tablet overcomes difficulties in swallowing a hard, solid tablet, especially for children and adults having small oral and pharyngeal cavities. One of skill in the art will understand that there are various methods to form a compactable granular formulation which depend on many factors including, for example, the selection of the specific forms of zinc, vitamins, minerals, and additives for the formulation. Conventional methods of combining the components of the formulation and other desired additives to form a compactable granular formulation may be used. For example, a compactable granular formulation may be formed by first blending the zinc with the desired vitamins, additional minerals, and suitable excipients to form a mixture. The compactable granular formulation may then be further processed using conventional techniques to form the final chewable tablet. For example, a compactable granular formulation may be compressed into a chewable tablet according to any technique known in the art, such as by placing the compactible granular formulation into a die and compressing the formulation into a chewable tablet having the desired shape and weight. An external lubricant may be applied to the wall of the die prior to adding the granular formulation. Further, the formulation may be compressed at a pressure and temperature suitable to form a chewable tablet with desired properties of strength, hardness, disintegration, and release of the formulation upon administration.

In certain embodiments, the present disclosure contemplates a formulation in a chewable tablet with excipients including sucrose, microcrystalline cellulose, vegetable stearic acid, orange flavor, vegetable magnesium stearate, calcium silicate, silicon dioxide, yellow #6 Lake, sucralose, and Stevia 98%.

In certain embodiments, the present disclosure contemplates a formulation in a water-miscible drop with excipients including, for example, MCT oil, xylitol, beeswax, natural flavors, polysorbate 80, mixed tocopherols (anti-oxidants), and sucralose.

In certain embodiments, the present disclosure contemplates a formulation with excipients such as, for example, starches, saccharides, fats, antioxidants, amino acids, proteins, and derivatives or combinations thereof. Antioxidants, for example, generally improve the stability of the formulation. Excipients may be added to chewable tablets, for example, which generally require acceptable softness, disintegration, and dissolution rates for release of the formulation, as well as suitable stability and size for effective delivery of the formulation. For aesthetic purposes, the formulation and/or vehicle may include excipients to appeal to the subject's senses, such as colorants, flavoring agents, fragrances, and texture modifiers.

In certain embodiments, the present disclosure contemplates a formulation wherein one or more lubricants may be added to inhibit sticking of the ingredients during their compression into a chewable tablet. Examples of suitable lubricants include, but are not limited to, stearic acid, palmitostearate, talc, and oils. Additionally, flavoring agents may be added to the formulation and/or vehicle, for example, fruit flavors, or sweeteners, such as sodium saccharin, aspartame, confectionery sugar, sorbitol, sucrose, xylitol, or combinations thereof. Further, the formulation may include disintegrants to facilitate the breakup of the formulation's vehicle, such as a soft gel, after it is administered to a subject. Examples of disintegrants include, but are not limited to, modified or unmodified starches such as corn starch, potato starch, or wheat starch, or croscarmellose sodium. Additionally, the formulation and/or vehicle may include suitable colorants, such as red beet powder, ferric oxides, FD & C dyes, or combinations thereof.

In certain embodiments, the present disclosure contemplates a kit containing a plurality of discrete dosage units of a formulation all contained in the same container or pack. In certain embodiments, the kit may contain discrete dosage units with different levels of Vitamin D. For example, the kit may contain discrete dosage units with a concentration of 3000 IUs Vitamin D and discrete dosage units with a concentration of 5000 IUs. Examples of suitable containers or packs include, but are not limited to, bottles, vials, blister packs, and pouches.

In certain embodiments, the present disclosure contemplates a method of treating malabsorption in a subject by the subject orally consuming a single dosage unit of a formulation once per day. In other embodiments, the subject consumes the formulation twice per day. In further embodiments, the method of treating malabsorption in a subject includes the subject swallowing a soft gel containing a formulation. In other embodiments, the method of treating malabsorption in a subject includes the subject chewing and swallowing a tablet containing a formulation. In further embodiments, the method of treating malabsorption in a subject includes placing a predetermined volume of a water-miscible formulation in the subject's mouth or on the subject's tongue.

The formulations contemplated by the present disclosure are advantageous for subjects with malabsorption by containing fat-soluble vitamins, at levels specifically-recommended for subjects with malabsorption, in single dose form. The single dose formulations contemplated herein, which may be in a kit, offer convenience, reduce a subject's pill burden, and allow for a simpler method of administration. For example, the methods contemplated by the present disclosure, such as the oral consumption of chewable tablets or water-miscible drops, are advantageous for subjects with malabsorption, who are often children who otherwise may struggle to swallow conventional tablets. Further, the lemon oil contained in the formulation reduces belching otherwise induced by fat-soluble vitamins contained in the formulation, further increasing the likelihood of compliance. Individually and collectively, these advantages increase the likelihood that a subject with malabsorption will comply with a recommended vitamin regimen.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The compositions, concentrations, and vehicles of the various embodiments described herein are exemplary. Various other compositions, concentrations, and vehicles for the formulations described herein are possible. Particular examples of embodiments contemplated by the present disclosure are described below.

Example 1

A Soft Gel Formulation was Formulated as Described Below

The formulation was encapsulated in a soft gel composed of gelatin, purified water, glycerin, soybean oil, natural lemon flavor, beeswax, soy lecithin, polysorbate 80, sucralose, and caramel color, which contained the ingredients as described in Table II, below.

TABLE II

Soft Gel Formulation Ingredients (per soft gel).

| Ingredient | Concentration |
| --- | --- |
| Vitamin A (12% Palmitate, 88% Beta-Carotene) | 16000 IUs |
| Vitamin C (Zinc ascorbate and Ascorbic Acid) | 100 mg |
| Vitamin D (as Cholecalciferol) | 1500 IUs |
| Vitamin E (as d-Alpha Tocopherol) | 200 IU |
| Vitamin K (as Phytonadione) | 800 mcg |
| Thiamin (as Thiamine Mononitrate) | 1.5 mg |
| Riboflavin (Vitamin B-2) | 1.7 mg |
| Niacin (as Niacinamide) | 20 mg |

TABLE II-continued

Soft Gel Formulation Ingredients (per soft gel).

| Ingredient | Concentration |
|---|---|
| Vitamin B-6 (as Pyridoxine HCL) | 1.9 mg |
| Folic Acid | 200 mcg |
| Vitamin B-12 (as Cyanocobalamin) | 6 mcg |
| Biotin | 100 mcg |
| Panthothenic Acid (as Calcium Pantothenate) | 12 mg |
| Zinc (as Zinc Ascorbate) | 10 mg |

Example 2

A Chewable Tablet Formulation was Formulated as Described Below

The formulation was created in a chewable tablet composed of sucrose, microcrystalline cellulose, vegetable stearic acid, orange flavor, vegetable magnesium stearate, calcium silicate, silicon dioxide, yellow #6 Lake, sucralose, and Stevia 98%, which contained the ingredients as described in Table III, below.

TABLE III

Chewable Tablet Ingredients (per tablet).

| Ingredient | Concentration |
|---|---|
| Vitamin A (12% Palmitate, 88% Beta-Carotene) | 16000 IUs |
| Vitamin C (Zinc ascorbate and Sodium Ascorbate) | 100 mg |
| Vitamin D (as Cholecalciferol) | 1500 IUs |
| Vitamin E (as d-Alpha Tocopherol) | 200 IU |
| Vitamin K (as Phytonadione) | 1000 mcg |
| Thiamin (as Thiamine Mononitrate) | 1.5 mg |
| Riboflavin (Vitamin B-2) | 1.7 mg |
| Niacin (as Niacinamide) | 10 mg |
| Vitamin B-6 (as Pyridoxine HCL) | 1.9 mg |
| Folic Acid | 200 mcg |
| Vitamin B-12 (as Cyanocobalamin) | 6 mcg |
| Biotin | 100 mcg |
| Panthothenic Acid (as Calcium Pantothenate) | 12 mg |
| Zinc (as Zinc Oxide and Zinc Ascorbate) | 15 mg |

Example 3

A Drop Formulation was Formulated as Described Below

The formulation was created in a drop formulation composed of MCT oil, xylitol, beeswax, natural flavors, polysorbate 80, mixed tocopherols (anti-oxidants), and sucralose, which contained the ingredients as described in Table IV, below.

TABLE IV

Drop Formulation Ingredients (per 1.0 mL).

| Ingredient | Concentration |
|---|---|
| Vitamin A (25% Palmitate, 75% Beta-Carotene) | 9254 IUs |
| Vitamin C (as Ascorbic Acid) | 90 mg |
| Vitamin D (as Cholecalciferol) | 1500 IUs |
| Vitamin E (as d-Alpha Tocopheryl Acetate) | 100 IU |
| Vitamin K (as Phytonadione) | 1000 mcg |
| Thiamin (Vitamin B-1 as Thiamine Mononitrate) | 1.0 mg |

TABLE IV-continued

Drop Formulation Ingredients (per 1.0 mL).

| Ingredient | Concentration |
|---|---|
| Riboflavin (Vitamin B-2) | 1.2 mg |
| Niacin (as Niacinamide) | 12 mg |
| Vitamin B-6 (as Pyridoxine HCL) | 1.2 mg |
| Vitamin B-12 (as Cyanocobalamin) | 4 mcg |
| Biotin | 30 mcg |
| Panthothenic Acid (as d-Calcium Pantothenate) | 6 mg |
| Zinc (from Zinc Gluconate) | 10 mg |

Example 4

A Method of Treating Malabsorption in a Subject as Described Below

A method for treating malabsorption in a subject, wherein the subject is a child between 1 and 3 years of age and is diagnosed with cystic fibrosis. A 1.0 mL oral dose of the drop formulation described in Example 3 above is administered daily to a subject, preferably taken with meals and supplemental pancreatic enzymes.

REFERENCES

1. Tanpricha V, et al. *J Clin Endocrinol Metab*, April 2012, 97(4) 1082-1093.
2. Holick M F, et al. *J Clin Endocrinol Metab*, July 2011, 96(7) 1911-1930.
3. Lam H S, et al. *Pediatrics*, August 2006, 118(2) 820-824.

Now, therefore, the following is claimed:

1. A formulation, comprising:
   at least 1500 IUs of Vitamin D;
   at least one additional fat-soluble vitamin;
   lemon oil; and
   zinc;
   wherein the formulation is encapsulated in a single soft gel.
2. The formulation of claim 1, wherein the concentration of vitamin D is at least 3000 IUs.
3. The formulation of claim 2, wherein the concentration of Vitamin D is about 3000 IUs.
4. The formulation of claim 2, wherein the concentration of Vitamin D is about 5000 IUs.
5. The formulation of claim 1, wherein the concentration of Vitamin K is greater than 800 mcg.
6. The formulation of claim 5, wherein the concentration of Vitamin K is about 1000 mcg.
7. The formulation of claim 5, wherein the concentration of Vitamin K is about 2000 mcg.
8. The formulation of claim 1, further comprising at least one water-soluble vitamin.
9. The formulation of claim 1, wherein the total volume of the soft gel is no greater than 2.0 mL.
10. The formulation of claim 1, wherein the total volume of the soft gel is no greater than 1.0 mL.
11. A formulation, comprising:
    at least 1500 IUs of Vitamin D;
    at least one additional fat-soluble vitamin;
    lemon oil; and
    zinc;
    wherein the formulation is in a water-miscible drop.

* * * * *